United States Patent [19]

DelliColli et al.

[11] 4,381,194

[45] Apr. 26, 1983

[54] ALKALI LIGNIN BASED PESTICIDE PHYTOTOXICITY REDUCING COMPOSITION

[75] Inventors: Humbert T. DelliColli, Hanahan; Thomas F. McPartland, Charleston Heights; Walter A. Bauer, Johns Island, all of S.C.

[73] Assignee: Westvaco Corporation, New York, N.Y.

[21] Appl. No.: 232,647

[22] Filed: Feb. 9, 1981

[51] Int. Cl.³ .......................................... A01N 25/12
[52] U.S. Cl. .......................................... 71/65; 71/79; 71/DIG. 1; 424/14; 424/16
[58] Field of Search .................. 71/DIG. 1, 65, 79; 424/14, 16

[56] References Cited

U.S. PATENT DOCUMENTS

| Re. 29,238 | 5/1977 | Dimitri et al. | 71/101 |
|---|---|---|---|
| 2,871,155 | 1/1959 | Klomparens et al. | 167/42 |
| 3,342,581 | 9/1967 | Woodward et al. | 71/65 |
| 3,726,850 | 4/1973 | Detroit | 260/124 A |
| 3,813,236 | 5/1974 | Allan | 71/94 |
| 3,929,453 | 12/1975 | Dimitri et al. | 71/101 |
| 3,954,439 | 5/1976 | Papamichael et al. | 71/93 |
| 3,984,225 | 10/1976 | Sears et al. | 71/25 |
| 3,992,532 | 11/1976 | Dimitri | 424/213 |
| 4,184,866 | 1/1980 | DelliColli et al. | 71/65 |
| 4,244,728 | 1/1981 | DelliColli et al. | 71/65 |
| 4,244,729 | 1/1981 | DelliColli et al. | 71/65 |

FOREIGN PATENT DOCUMENTS 619202 12/1962 Belgium.
1952910 6/1970 Fed. Rep. of Germany.

OTHER PUBLICATIONS

Belgian Patent 782,120 Discussed by G. R. Stephenson and F. Y. Chang in Paper "Comparative Activity and Selectivity of Herbicide Antidotes," *Chemistry and Action of Herbicide Antidotes* (Academic Press 1978), pp. 36, 48, 56 and 60.

*Primary Examiner*—Catherine L. Mills
*Attorney, Agent, or Firm*—Terry B. McDaniel; Richard L. Schmalz

[57] ABSTRACT

A method for protecting crops from injury caused by the application of herbicides and fungicides has been discovered, the method comprising applying to the crops in combination with the pesticide a phytotoxicity reducing amount of a water-insoluble, non-sulfonated alkali lignin. A water-insoluble, non-sulfonated alkali lignin based spray tank mix additive is provided which, when mixed with the pesticide prior to application, reduces the phytotoxic effect of the pesticide.

29 Claims, No Drawings

ALKALI LIGNIN BASED PESTICIDE PHYTOTOXICITY REDUCING COMPOSITION

BACKGROUND OF THE INVENTION

1. Field of the Invention

This invention relates to a method of protecting crops from injury caused by application of herbicides and fungicides. More particularly, this invention relates to a method of applying to the crops in combination with the herbicides or fungicides an alkali lignin spray tank mix additive whose primary purpose is the reduction of phytotoxic effects of the herbicide or fungicide.

2. Description of the Prior Art

Chemical pesticides play a major role in promoting high crop yields. They also replace more expensive labor and mechanical methods for weed and pest control. For maximum utility in crop production, pesticides must have a high degree of selective toxicity, i.e., injury to undesirable plant species, fungi, and other pests but not to the desirable crops.

Selectivity may be governed by one or more factors including pesticide penetration, uptake, translocation, and metabolism. In some cases a crop is only marginally tolerant to herbicides required for the major weed problems and crop injury can often occur due to unusual weather conditions, interactions with other chemicals, crop varietal differences or errors in application. In the absence of a high degree of selective toxicity, steps must be taken to protect the desirable crop from the phytotoxic effect of the pesticide. An added degree of selectivity can often be achieved by critical timing of application, suitable placement of the pesticide, or use of chemical safening agents with the pesticide.

Although activated charcoal was perhaps the first material used as a pesticide safener, Belgian Pat. No. 619,202, in 1962, introduced the antidote concept. In this patent, Hoffman reduced carbamate herbicide damage to young grain plants by treating the seeds prior to planting with a non-phytotoxic amount of a hormone type growth regulant such as 4'-chloro- or 3',4'-dichloro-2-hydroxyiminoacetanilide. Also, Hoffman disclosed treating cereal seeds with nonphytotoxic amounts of 1,8-naphthalic anhydride to protect them from various herbicides in German Offenlegungsschrift No. 1,952,910.

Belgian Pat. No. 782,120, in 1972 disclosed N,N-diallyl-2,2-dichloroacetamide as an antidote-safener for thiocarbamate herbicide. This material may be included in the herbicide formulation and applied with the herbicide treatment. Subsequently, various other compounds have been found to be antidote-safeners for herbicides. However, such antidotes chemically modify the pesticides to counteract its poisonous effects. In a broader context a pesticide safener is any substance which prevents objectionable changes to the crop upon exposure to the pesticide. Thus, a safener, or phytotoxicity reducer, is not necessarily an antidote.

It is the general object of this invention to provide a lignin based pesticide safener which inhibits the exposure of the pesticide to reduce its phytotoxic effects.

The use of lignins in pesticide formulations as a surfactant or as part of the pesticide delivery system is known.

In U.S. Pat. No. 3,726,850, Detroit teaches water-soluble, ozone-oxidized alkali lignin to be pesticide dispersants. U.S. Pat. No. 3,992,532 discloses a method for providing a flowable pesticide formulation with such rheological properties so as to reduce or eliminate sedimentation and liquid phase separation of insoluble pesticides by mixing alkali lignin and liquid toxicant with a hydrocarbon oil and subjecting the mixture to high shear.

U.S. Pat. No. 3,813,236 discloses the chemical covalent bonding of a pesticide to a lignin polymeric substrate. The pesticide is controllably released by destruction of the covalent chemical bonds. U.S. Pat. No. 3,929,453, reissued as Re 29,238, teaches a slow release lignin composite obtained by the coprecipitation-inclusion from an aqueous alkaline lignin solution by adding acid or salts, the drying of a precipitated lignin slurry/pesticide dispersion, or the elimination of a common solvent from a lignin-pesticide mixture.

In other sustained release compositions, U.S. Pat. Nos. 4,184,866, 4,244,728 and 4,244,729, all of which have as a co-inventor a co-inventor in this application, teach an improved pesticide carrier made by cross-linking an alkali lignin with epichlorohydrin or formaldehyde.

It is the particular object of this invention to provide an alkali lignin-pesticide combination suitable for spray application which combination has a reduced phytotoxic effect than that resulting from application of the pesticide alone. It is a further object of this invention to provide a water-insoluble alkali lignin based spray tank mix additive which, when mixed with the pesticide prior to application, reduces the phytotoxic effect of the pesticide. It is a still further object of the invention to provide a method for protecting crops from injury caused by application of a pesticide selected from the group consisting of herbicides, fungicides and insecticides, the method comprising applying to the crops in combination with the pesticide a phytotoxicity reducing amount of water-insoluble alkali lignin.

SUMMARY OF THE INVENTION

A method for protecting crops from injury caused by the application of herbicides and fungicides has been discovered, the method comprising applying to the crops in combination with the pesticide a phytotoxicity reducing amount of a water-insoluble, non-sulfonated alkali lignin. A water-insoluble, non-sulfonated alkali lignin based spray tank mix additive is provided which, when mixed with the pesticide prior to application, reduces the phytotoxic effect of the pesticide.

DESCRIPTION OF THE PREFERRED EMBODIMENTS

The water-insoluble, non-sulfonated alkali lignin of the invention is obtained from the alkaline solution, or black liquor, recovered from the alkali digestion of lignocellulosic materials. Alkali lignins are sulfate (kraft) lignins or soda lignins, depending on the digestion process used. In the sulfate, or kraft, process, the wood chips are digested in a solution containing sodium hydroxide and sulfide; whereas, in the soda process, a solution of sodium hydroxide alone is used. The sulfate process may be carried out continuously in a Kamyr digester, or batchwise. The alkali lignin may be recovered from the black liquor by several different methods. For example, the lignin-containing alkaline solution may be treated with acid so that a sodium lignate product, designated as "C", precipitates out, is filtered and dried. Alternatively, the filtered precipitate can be washed and purified with water to make a sodium lignate product designated as "B". Or, the filtered precipitate can be washed with water, treated with about a 15% sulfuric acid solution, washed again with water and dried to produce a lignin product designated as "A". It is in this manner that the commercial products Indulin® C, Indulin® B and Indulin® A, respectively, are produced by Westvaco Corporation. The water-insoluble lignin of this invention is the modified "A" lignin. Both the "B" lignin and "C" lignin are water soluble.

The water-insoluble alkali lignin can be combined with an herbicide or fungicide to effectively reduce phytotoxicity by adjusting the lignin-to-pesticide ratio. Also, it may be desirable to combine the lignin with more than one herbicide or fungicide for a single application. An effective phytotoxicity reducing amount of lignin additive for most fungicides and herbicides is provided by a pesticide-to-lignin ratio of 1–10:10–1. Optimum phytotoxicity reduction with individual herbicides and fungicides can be achieved by adjustments within this range. The preferred herbicides are: metribuzin; metribuzin and alachlor; atrazine; alachlor; atrazine and alachlor; metolochlor; butylate and cyanazine. The preferred fungicides are: benomyl; aqueous copper; thiabendazol; triphenyl tin hydroxide (TPTH); TPTH and sulfur; carboxin; pentachloronitrobenzene (PCNB); captafol; chlorothalonil; and dicloran.

The water-insoluble alkali lignin-pesticide composite can be formulated by the manufacturer by wet grinding a slurry of the granular lignin and herbicide or fungicide to the desired average particle size of from 3 to 9 microns in diameter and packaging the wettable powder formulation in a single container for immediate application.

Also, it is practical to formulate the lignin separately as a suspension concentrate to be combined with the pesticide by the applicator in a single spray tank mix prior to application. The pseudoplastic suspension concentrate of water-insoluble alkali lignin is prepared in water with minor amounts of selected conventional surfactants including humectants, wetting agents, dispersing agents and/or antifreeze agents. To achieve the desired dispersed suspension, the granular lignin is ground or milled to a powder with a mean particle size of a particle diameter of from 0.5 to 5.0 microns, as determined by dark field microscope.

The utilization of supplemental agents having wetting, dispersing and/or suspending properties is widespread in the preparation of formulations containing water-insoluble powders such as herbicides, fungicides and other industrially employed powders, to render the powders dispersible in water. Ideally, the wettable powder formulations are fast wetting when dispersed in water and form suspensions with relatively high solids content which are low foaming and do not exhibit tendencies toward sedimentation with age. Satisfactory humectants employed in the water-insoluble, non-sulfonated alkali lignin suspension concentrate are glycerol, saccharinic acids and ethoxylated glycerides, with glycerol being preferred. Various commercially available soaps, detergents and surface active agents may be employed as a wetting agent. One or more of the following are preferred: di 2-ethylhexyl sodium sulfosuccinate, sodium 2-ethyl sulfate and mixtures thereof, sold under the trade names ROE 55 and Valchem 329-104. Suitable dispersing agents are water-soluble lignin sulfonates and alkyl naphthalene sulfonates. Water-soluble sulfonated lignins can be lignosulfonates from the sulfite process of wood pulping or an alkali salt of a sulfate lignin which has been sulfonated, such as Polyfon H, sold by Westvaco Corporation. Likewise, the alkyl naphthalene sulfonates are well known in the art and are used in the form of their alkali metal or ammonium salt.

To lower the freezing point of the aqueous suspension, antifreeze agents such as propylene glycol, methanol and ethylene glycol are employed, with propylene glycol being preferred.

As can be appreciated by those in the art, in preparing the flowable formulations of the present invention, supplemental agents functioning as water-conditioning agents, thickening agents, and the like suitably may be added.

In preparing the flowable formulations of the invention, the ingredients employed suitably may be combined in various sequences in conventional mixing means. However, it is usually necessary to add at least a portion of one of the liquid ingredients to the granular water-insoluble alkali lignin prior to introduction into the ball mill, as it is difficult to achieve the desired lignin particle size in a dry grind.

The invention having been broadly described, the examples to follow are given to show specific embodiments thereof.

The water-insoluble alkali lignin-pesticide wettable powder formulation of this invention is prepared by combining one or more of the herbicides or fungicides with the lignin in an aqueous slurry and drying the slurry to from about 2% to about 5% moisture. Add from about 1% to about 10% by volume of one or more of the conventional surfactants listed above to the essentially dry slurry and grind the slurry to an average particle size of from 3 to 9 microns in diameter by attrition grinding. The preferred surfactants are a mixture of wetting agents (di 2-ethylhexyl sodium sulfosuccinate and sodium 2-ethyl sulfate) and a dispersing agent (water-soluble lignin sulfonate).

EXAMPLE 1

To determine the phytotoxicity reduction from applying a formulation where the pesticide is interground with the water-insoluble alkali lignin, the fungicide PCNB was formulated with a water-insoluble kraft lignin according to the above preferred procedure in fungicide/lignin/surfactant ratios of 50:47:3 and 75:22:3. The formulations were applied to tomatoes (Walter variety, unstaked) by directed basal spray at blossom set at rates of 10 and 20 lbs. active ingredient per acre delivered in 60 gallons per acre. The yield data are presented in Table I.

TABLE I

| Formulation | Fungicide Rate (Lbs./ Acre) | Total Yield (Fruit/ 10 Plants) | % Reject | Commercial Harvest Data 1,000 Lbs./ Acre |
|---|---|---|---|---|
| 50% PCNB | 10 | 631 | 1.9 | 17.5 |
| 50% PCNB | 20 | 708 | 2.3 | 19.7 |
| 75% PCNB | 10 | 772 | 2.7 | 22.6 |
| 75% PCNB | 20 | 743 | 2.6 | 28.4 |
| PCNB Alone* | 10 | 526 | 3.8 | 15.8 |
| PCNB Alone* | 20 | 500 | 2.2 | 12.0 |
| No Treatment | | 609 | 19.6 | 14.6 |

*Commercial formulation

Here the data on Table I shows for the third consecutive year that the kraft lignin-based formulations resulted in enhanced yields of marketable fruit as indicated by both 10 plant statistical data and commercial harvest indicators, 1,000-pound pallet boxes of saleable fruit. The lowest yields observed came from plots treated with the commercial 75% PCNB at 10 and 20 pounds of active ingredient per acre.

A preferred procedure for formulating the water-insoluble alkali lignin suspension concentrate is as follows (All portions are based on total formulation volume.):

(a) After dissolving 2 parts by Polyfon H in 57 parts water in a mix tank, add to the mixture approximately 4 parts of wetting agent ROE-55 and/or Valchem 329-104.

(b) Upon addition of 34 parts of a water-insoluble kraft lignin, the slurry is subjected to a grinding operation by circulating through an attritor. The time for the grinding operation is from 1 to 8 hours.

(c) About one hour prior to completion of the grind, add about 2 parts of propylene glycol and about 1 part glycerol.

The lignin suspension concentrate is combined with a pesticide prior to application in the following manner:

(a) The lignin slurry is added with agitation to 3-5 gallons of water at a rate to produce about 1 to 4 pints of lignin additive per acre, and the resultant slurry is added to a mix tank ¼ to ⅓ full of water;

(b) The formulated pesticide is added in accordance with the manufacturer's instructions; and, (c) Water is added to produce the desired volume of spray carrier per acre.

EXAMPLE 2

A 4 lb. per gallon water-insoluble kraft lignin flowable suspension concentrate was prepared in a manner similar to that described above and combined at various ratios with the fungicide PCNB to test for phytotoxicity reduction on tomatoes (Walter variety, unstaked). The fungicide was applied as a basal spray at blossom set at both 10 and 20 pounds per acre, and the lignin flowable rates were varied from 0 to 8 pints per acre. The amounts of lignin flowable were first dispersed in five gallons of water and added to the 500 gallon spray tank, which was one-fourth to one-third full of water. Then the pre-slurried PCNB was added to the desired spray volume (60 gallons per acre), and the lignin-fungicide composition was applied. The yield data is shown in Table II.

TABLE II

| Lignin Flowable Dose Rate (Pints/ Acre) | PCNB Application Rate (Lbs. a.i./ Acre) | Lignin/ Fungicide Ratio | Total Yield (Fruit/10 Plants) | Acceptable Yield (Fruit/10 Plants) | % Reject |
|---|---|---|---|---|---|
| 0 | 10 | — | 426 | 410 | 3.8 |
| 1 | 10 | 1/20 | 488 | 472 | 3.3 |
| 2 | 10 | 1/10 | 510 | 500 | 2.0 |
| 3 | 10 | 3/20 | 548 | 538 | 1.8 |
| 4 | 10 | 2/10 | 560 | 554 | 1.8 |
| 8 | 10 | 2/5 | 560 | 546 | 3.4 |
| 0 | 20 | — | 500 | 489 | 2.2 |
| 1 | 20 | 1/40 | 506 | 490 | 3.2 |
| 2 | 20 | 1/20 | 572 | 570 | 0.4 |
| 3 | 20 | 3/40 | 562 | 546 | 2.9 |
| 4 | 20 | 1/10 | 588 | 576 | 2.1 |
| 8 | 20 | 1/5 | 584 | 580 | 0.9 |
| 2 | 0 | — | 592 | 472 | 20.3 |
| 0 | 0 | — | 609 | 509 | 19.6 |

The data in Table II indicates that as the dosage of lignin flowable increased from 0 pints to a maximum of 8 pints per acre, total yields increased from 426 fruit per 10 plants to 560 fruit in the presence of ten pounds of active PCNB per acre. A similar situation occurred when the PCNB was applied at 20 pounds. Here, however, one pint of PC-671 had no effect. In both cases, no difference was seen when the dosage of lignin safener was increased from four to eight pints per acre.

Control data shows no difference in biological control between a lignin without active ingredient treatment and a treatment consisting of neither lignin nor active fungicide.

EXAMPLE 3

In a similar manner as in Example 1, the water-insoluble kraft lignin flowable was combined in the spray tank mix with the fungicides captafol, chlorothalonil and benomyl, individually, and applied as a foliar spray at blossom set to tomato plants (908 variety, unstaked). The yield data from these tests are presented in Table III. All fungicides were applied at rates indicated on their respective labels.

TABLE III

| Treatment | Lignin Flowable Dose Rate (Pints/ Acre) | Lignin/ Fungicide Ratio | Total Yield (Fruit/10 Plants) | Acceptable Yield (Fruit/10 Plants) | % Reject |
|---|---|---|---|---|---|
| Captafol | 0 | — | 514 | 452 | 12.1 |
|  | 2 | 3/2 | 673 | 626 | 7.5 |
| Chlorothalonil | 0 | — | 596 | 555 | 6.9 |
|  | 2 | 1/1 | 693 | 668 | 3.6 |
| Benomyl | 0 | — | 428 | 401 | 6.7 |
|  | 2 | 1/2 | 441 | 416 | 5.6 |
| none* |  |  | 397 | 364 | 5.7 |

*Black Plastic Mulch

The data in Table III show that significant yield increases were observed with captafol and chlorothalonil when the kraft lignin flowable was used at two pints per acre. In all cases, the data point to the possibility of some performance enhancement as indicated by increased yields and lower reject levels where lignin was present. All chemical treatments resulted in higher total yields than the black polyethylene mulch used as a control.

EXAMPLE 4

The herbicide metribuzin (known to cause damage to varieties of soybeans when applied to light, sandy soils) was applied at the rate of one pound active ingredient per acre without lignin and in combination with one and two pints of the water-insoluble lignin flowable concentrate (one-half and one pound of lignin, respectively). Also, a control plot was prepared without herbicide and/or lignin where manual weed control was employed. The soil was a light, sandy loam with an organic matter level of 0.8%, and the earlier described procedure for tank mixing was used with a spray volume of 25 to 30 gallons per acre. The herbicide treatment was a pre-emergence regimen with application taking place within twelve hours of planting.

Emergence of the soybean seedlings, Bragg variety, occurred approximately ten days after planting. For about two to three weeks after emergence, all plots appeared to be similar in size, degree of viability, and proximity to competitive vegetation. Examination of these same plots eight weeks after emergence did, however, show a difference. The plots treated with metribuzin plus one pint of lignin flowable, metribuzin plus one quart of lignin flowable, and the hand-weeded check plot appeared to be similar in size (45-50 inches tall), with only minor appearance differences (based upon visual observations). The test plot, treated with only metribuzin at one pound per acre, revealed an average plant height of 20-25 inches.

Yield data were collected at harvest, as shown in Table IV.

TABLE IV

| Treatment | Lignin Flowable Dose Rate (Pints/Acre) | Lignin/Herbicide Ratio | Yield (Bu./Acre) | Average Bean* Wt. (mg) |
|---|---|---|---|---|
| Metribuzin | 0 | — | 26.4 | 152** |
| 1 lb. a.i./Acre | 1 | 1/2 | 28.7 | 174 |
|  | 2 | 1/1 | 67.0 | 201 |
| Control (no herbicide, manual weed control) | 0 | — | 61.0 | 193 |

*Average of 10,000 individual beans; all beans were dried to 15% moisture.
**Beans from this plot showed a greenish coloration after drying. The plot averaged 25-30% empty pods.

Yields ranged from approximately 26 bushels/acre (metribuzin alone) to 67 bushels/acre (metribuzin plus one quart of lignin flowable) with the hand-weeded check producing an estimated 61 bushels/acre. The weights of the individual bean also varied from a minimum of 152 mg. to a high of 201 mg. As indicated on the data table, the plants from the metribuzin-only plot bore 25% to 30% empty pods and the beans collected showed a green coloration as well as many morphological deformations. These criteria can be assumed to be due to premature ripening which may have been brought about by the metribuzin.

EXAMPLE 5

To assess the performance of the water-insoluble alkali lignin suspension as a safener for the herbicide combination of atrazine and alachlor on field corn, three field plots ranging in size from 2.5 to 7.5 acres were pre-emergence treated with herbicide tank mix at the label recommended rate. One plot received no lignin additive and was used as a control while the other two plots received one quart and two quarts per acre, respectively.

Total field rather than small plot or single row harvest was selected because of wide variations in soil type and land elevation within each treatment zone. Field areas assigned to the treatment were selected so that each treatment covered essentially the same soil types, moisture levels, and elevation. Therefore, total field harvest was designed to minimize field condition variation within each field and test area layout and to encompass the same type of variation between fields in order to provide yield data representative of large scale agriculture.

Harvest data are presented in Table V.

TABLE V

| Treatment | Lignin/Herbicide/Herbicide Ratio | Plot Size (Acre) | Yield (Bu./Acre) |
|---|---|---|---|
| alachlor/atrazine | 0/1/1 | 2.5 | 57 |
| alachlor/atrazine + 1 qt. lignin/acre | 1/2/2 | 4.5 | 94 |
| alachlor/atrazine + 2 qts. lignin/acre | 1/1/1 | 7.5 | 93 |

Prior to harvest, periodic monitoring of the test sites was carried out. This procedure consisted of plant samplings used in the determination of pre-harvest yield estimates and was initiated when cob formation was noted in all these test areas. Early data revealed major differences in total cob weight between all three treatment zones, but as the season progressed, the difference between the one and two-quart/acre sites grew smaller while those between 0 and one-quart/acre remained sizeable. In fact, a statistically insignificant difference between yields from the one and two quarts/acre plots was predicted about three weeks before actual harvest. The harvest data indicate 39% bushel per acre yield increase when lignin is used in conjunction with the alachlor/atrazine herbicide treatment over the herbicide treatment alone.

It will be understood that the examples are given for illustration purposes and not by way of limitation.

We claim:

1. In a method of protecting crops from injury caused by application to the crops of one or more pesticides selected from the group consisting of herbicides and fungicides, in combination with a lignin, the improvement of forming the combination by
   (a) forming a pseudoplastic aqueous suspension concentrate of a water-insoluble alkali lignin containing minor amounts of at least one surfactant selected from the group consisting of humectants, wetting agents, dispersing agents and anti-freeze agents wherein the lignin has a mean particle size of from 0.5 to 5 microns in diameter, and
   (b) combining a phytotoxicity reducing amount of the lignin suspension concentrate with the pesticide prior to the application.

2. The method of claim 1 wherein the pesticide to lignin ratio is 1-10:10-1.

3. The method of claim 1 wherein the herbicide is selected from the group consisting of metribuzin, metribuzin and alachlor, atrazine, alachlor, atrazine and alachlor, metolochlor, butylate, and cyanazine.

4. The method of claim 1 wherein the fungicide is selected from the group consisting of benomyl, aqueous copper, thiabendazol, triphenyl tin hydroxide, triphenyl tin hydroxide and sulfur, carboxin, PCNB, captafol, chlorothalonil, an dicloran.

5. The method of claim 1 wherein the humectant is selected from the group consisting of glycerol, saccharinic acids and ethoxylated glycerides.

6. The method of claim 1 wherein the wetting agent is selected from the group consisting of di 2-ethylhexyl sodium sulfosuccinate, sodium 2-ethyl sulfate and mixtures thereof.

7. The method of claim 1 wherein the dispersing agent is a water-soluble lignin sulfonate or alkyl naphthalene sulfonate.

8. The method of claim 1 wherein the antifreeze agent is selected from the group consisting of propylene glycol, methanol and ethylene glycol.

9. The method of claim 1 wherein the water-insoluble alkali lignin is ground to an average particle size of from 0.5 to 5 microns in diameter.

10. The method of claim 1, 2, 3, 4, 5, 6, 7, 8, or 9 wherein the water-insoluble alkali lignin is kraft lignin.

11. In a method of protecting crops from injury caused by application to the crops of a pesticide wherein the pesticide is a herbicide or fungicide, in combination with a lignin, the improvement of forming the combination by
   (a) combining a phytotoxicity reducing amount of a water-insoluble alkali lignin with the herbicide or fungicide in an aqueous slurry,
   (b) drying the slurry to from about 2% to about 5% moisture,
   (c) adding to the essentially dried slurry at least one surfactant selected from the group consisting of humectants, antifreeze agents, wetting agents and dispersing agents in an amount totaling from about 1% to about 10% by volume of the total formulation, and
   (d) grinding the slurry to a wettable powder with an average particle size of from 3 to 9 microns in diameter.

12. The method of claim 11 wherein the herbicide is selected from the group consisting of metribuzin, metribuzin and alachlor, atrazine, alachlor, atrazine and alachlor, metolochlor, butylate, and cyanazine.

13. The method of claim 11 wherein the fungicide is selected from the group consisting of benomyl, aqueous copper, thiabendazol, triphenyl tin hydroxide, triphenyl tin hydroxide and sulfur, carboxin, PCNB, captafol, chlorothalonil, and dicloran.

14. The method of claim 11 wherein the surfactants are a water-soluble lignin sulfonate and a mixture of di 2-ethylhexyl sodium sulfosuccinate and sodium 2-ethyl sulfate.

15. The method of claim 11 wherein the wettable powder is comprised of about 50% herbicide or fungicide, about 47% water-insoluble alkali lignin and about 3% surfactant.

16. The method of claim 11 wherein the wettable powder is comprised of about 75% herbicide or fungicide, 22% water-insoluble alkali lignin and about 3% surfactants.

17. The method of claim 11, 12, 13, 14, 15 or 16 wherein the water-insoluble alkali lignin is kraft lignin.

18. In a flowable pesticide formulation comprising one or more herbicides or fungicides, a water-insoluble alkali lignin, and at least one surfactant selected from the group consisting of humectants, anti-freeze agents, wetting agents and dispersing agents in an amount totaling from about 1% to about 10% by volume of the total formulation the improvement of grinding a phytotoxicity reducing amount of the lignin granules together with the herbicide or fungicide powders in the presence of at least one of the surfactants to an average particle size of from 3 to 9 microns.

19. The pesticide formulation of claim 18 wherein the herbicide is selected from the group consisting of metribuzin, metribuzin and alachlor, atrazine, alachlor, atrazine and alachlor, metolochlor, butylate, and cyanazine.

20. The pesticide formulation of claim 18 wherein the fungicide is selected from the group consisting of benomyl, aqueous copper, thiabendazol, triphenyl tin hydroxide, triphenyl tin hydroxide and sulfur, carboxin, PCNB, captafol, chlorothalonil, and dicloran.

21. The pesticide formulation of claim 18 wherein the humectant is selected from the group consisting of glycerol, saccharinic acids and ethoxylated glycerides.

22. The pesticide formulation of claim 18 wherein the wetting agent is selected from the group consisting of di 2-ethylhexyl sodium sulfosuccinate, sodium 2-ethyl sulfate and mixtures thereof.

23. The pesticide formulation of claim 18 wherein the dispersing agent is selected from the group consisting of a water-soluble lignin sulfonate or alkyl naphthalene sulfonate.

24. The pesticide formulation of claim 18 wherein the antifreeze agent is selected from the group consisting of propylene glycol, methanol and ethylene glycol.

25. The pesticide formulation of claim 18, 19, 20, 21, 22, 23 or 24 wherein the water-insoluble alkali lignin is kraft lignin.

26. The pesticide formulation of claim 18 wherein the herbicide is PCNB, the water-insoluble alkali lignin is kraft lignin, the surfactants are a mixture of wetting agents and dispersing agent di 2-ethylhexyl sodium sulfosuccinate, sodium 2-ethyl sulfate and a water-soluble lignin sulfonate.

27. The pesticide formulation of claim 18 wherein pesticide to lignin to surfactant ratio is 50:47:3.

28. The pesticide formulation of claim 18 wherein pesticide to lignin to surfactant ratio is 75:22:3.

29. The pesticide formulation of claim 18 wherein the pesticide-to-lignin ratio is 1–10:10–1.